(12) United States Patent
Bongers et al.

(10) Patent No.: US 10,866,147 B2
(45) Date of Patent: Dec. 15, 2020

(54) HEAT-FLOW SENSOR

(71) Applicant: KONINKLIJKE PHILIPS N.V., Eindhoven (NL)

(72) Inventors: Edwin Gerardus Johannus Maria Bongers, Thorn (NL); Louis Nicolas Atallah, Boston, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 259 days.

(21) Appl. No.: 15/781,867

(22) PCT Filed: Dec. 21, 2016

(86) PCT No.: PCT/EP2016/082200
§ 371 (c)(1),
(2) Date: Jun. 6, 2018

(87) PCT Pub. No.: WO2017/108964
PCT Pub. Date: Jun. 29, 2017

(65) Prior Publication Data
US 2018/0364109 A1 Dec. 20, 2018

(30) Foreign Application Priority Data
Dec. 21, 2015 (EP) .................................... 15201450

(51) Int. Cl.
*G01K 17/00* (2006.01)
*G01K 7/00* (2006.01)
(Continued)

(52) U.S. Cl.
CPC .............. *G01K 13/002* (2013.01); *A61B 5/01* (2013.01); *G01K 1/165* (2013.01); *G01K 7/427* (2013.01);
(Continued)

(58) Field of Classification Search
USPC ................... 374/183, 29, 208, 141, 166, 110
See application file for complete search history.

(56) References Cited

U.S. PATENT DOCUMENTS 5,711,604 A   1/1998  Nakamura
5,816,706 A * 10/1998  Heikkila .................. G01K 1/16
                                                              374/134
(Continued)

FOREIGN PATENT DOCUMENTS

JP          8304144 A    11/1996
JP       2012112767 A     6/2012
(Continued)

OTHER PUBLICATIONS

Kitamura, et al., "Development of a new method for the noninvasive measurement of deep body temperature without a heater", Medical Engineering & Physics, vol. 32, No. 1, Oct. 1, 2010, pp. 1-6.
(Continued)

*Primary Examiner* — Mirellys Jagan

(57) ABSTRACT

The invention describes a passive heat-flow sensor (1) comprising a contact face (11) for placement on a subject (8) during a temperature monitoring procedure; and a plurality of combined thermistor arrangements, wherein a combined thermistor arrangement comprises an inner thermistor (S1) arranged at an inner face of the sensor (1); an upper thermistor (S2) arranged at the upper surface of the sensor (1) and arranged relative to the inner thermistor (S1) to measure a vertical heat flow outward from the subject (8); and a lateral thermistor (S3) arranged relative to the inner thermistor (S1) to measure a horizontal heat flow along the contact face (11). The invention further describes a method of measuring the temperature of a subject (8) using a heat-flow sensor (1); and a temperature sensing arrangement (10) for monitoring the temperature of a subject (8) using a heat-flow sensor (1).

12 Claims, 4 Drawing Sheets

(51) Int. Cl.
*G01K 3/00* (2006.01)
*G01K 1/00* (2006.01)
*G01K 13/00* (2006.01)
*A61B 5/01* (2006.01)
*G01K 1/16* (2006.01)
*G01K 7/42* (2006.01)
*A61B 5/00* (2006.01)

(52) U.S. Cl.
CPC ........... *A61B 5/002* (2013.01); *A61B 2505/05* (2013.01); *A61B 2562/0271* (2013.01); *A61B 2562/046* (2013.01)

(56) References Cited

U.S. PATENT DOCUMENTS

| | | | | |
|---|---|---|---|---|
| 6,220,750 | B1 * | 4/2001 | Palti | G01K 1/16 374/164 |
| 6,735,379 | B2 * | 5/2004 | Salmon | A61F 7/00 374/121 |
| 7,354,195 | B2 * | 4/2008 | Sakano | G01K 1/024 340/870.17 |
| 8,057,093 | B2 * | 11/2011 | Sattler | G01K 1/16 374/100 |
| 2006/0056487 | A1 * | 3/2006 | Kuroda | G01K 13/002 374/179 |
| 2006/0173375 | A1 | 8/2006 | Koch | |
| 2010/0121217 | A1 | 5/2010 | Padiy et al. | |
| 2011/0158284 | A1 | 6/2011 | Goto | |
| 2011/0317737 | A1 | 12/2011 | Klewer et al. | |
| 2012/0024833 | A1 | 2/2012 | Klewer et al. | |
| 2012/0109571 | A1 | 5/2012 | Shimizu | |
| 2012/0128024 | A1 | 5/2012 | Tsuchida et al. | |
| 2014/0221796 | A1 | 8/2014 | Lia et al. | |
| 2015/0313474 | A1 | 11/2015 | Goto | |

FOREIGN PATENT DOCUMENTS

| | | |
|---|---|---|
| WO | 2010103436 A1 | 9/2010 |
| WO | 2011012386 A1 | 2/2011 |
| WO | 2013121762 A | 8/2013 |

OTHER PUBLICATIONS

Harper, et al., "Maintaining perioperative normothermia", downloaded from bmj.com, BMJ, vol. 326, Apr. 5, 2003, pp. 721-722.

Brandt, et al., "Diagnosis, prevention and treatment of accidental and perioperative hypothermia", Diagnosis, prevention and treatment of hypothermia, Biomed Tech 2012, 57(5), pp. 307-322.

Gunga, et al., "A new non-invasive device to monitor core temperature on earth and in space", Sitzungsberichte der Leibniz-Sozietät der Wissenschaften zu Berlin, 114(2012), pp. 67-79.

D. Sessler, "Perioperative Thermoregulation", American Society of Anesthesiologists, APSF 25th Anniversary edition, pp. 34-43.

Kimberger, et al., "The accuracy of a disposable noninvasive core thermometer", Reports of Original Investigations, Can J Anesth/J Can Anesth (2013) 60: pp. 1190-1196.

* cited by examiner

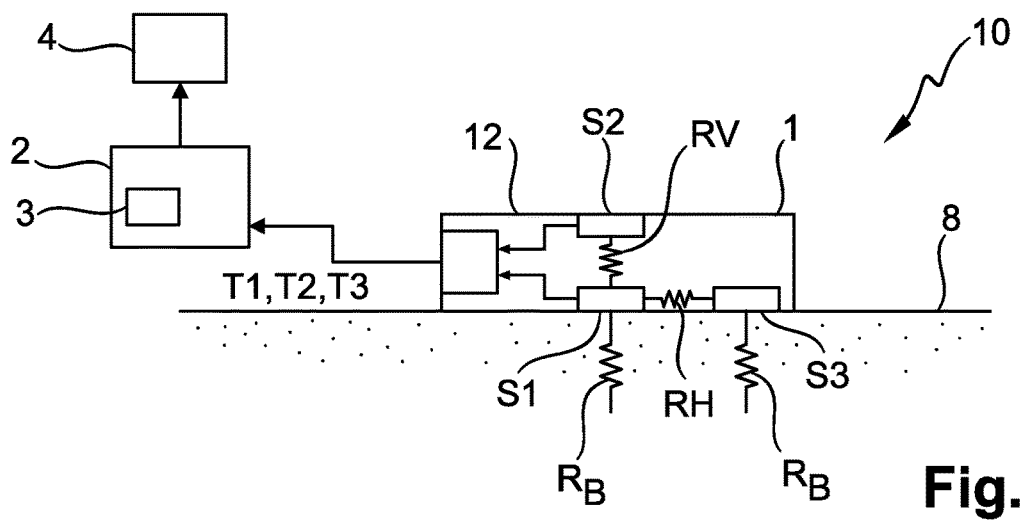
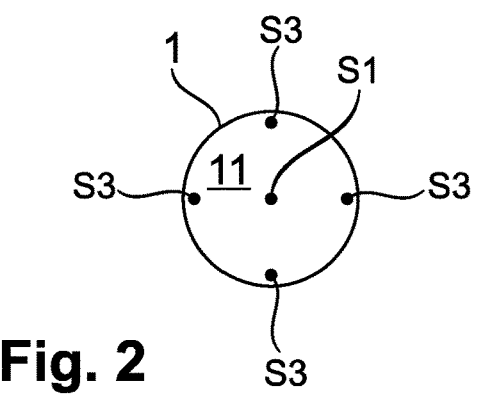
Fig. 2
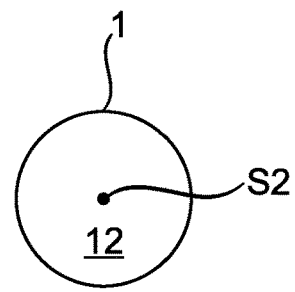
Fig. 3
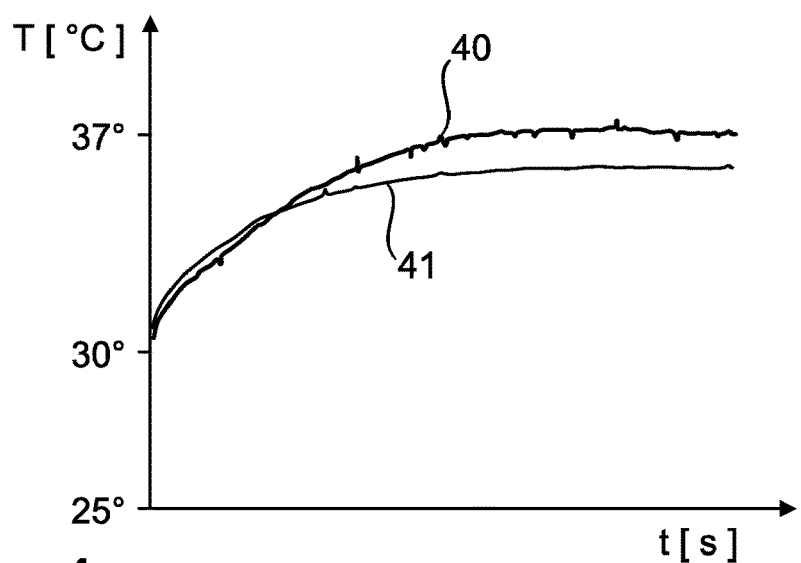
Fig. 4

HEAT-FLOW SENSOR

This application is the U.S. National Phase application under 35 U.S.C. § 371 of International Application No. PCT/EP2016/082200, filed on Dec. 21, 2016, which claims the benefit of European Application Serial No. 15201450.2, filed Dec. 21, 2015. These applications are hereby incorporated by reference herein.

FIELD OF THE INVENTION

The invention relates to a heat-flow sensor, a method of measuring the temperature of a subject using a heat-flow sensor, and a temperature sensing arrangement.

BACKGROUND OF THE INVENTION

Core body temperature (CBT) is an important vital sign in medical environments. A patient under anaesthetic is unable to regulate his/her body temperature, and operating rooms are generally cooled to a low level. Hypothermia occurs when the body core temperature drops below 36° C. to a potentially dangerous level. Surgical patients are often hypothermic upon leaving the operating room. Hypothermic patients run the risk of heart complications, especially during the first 24 hours after surgery, since hypothermia acts as a shock to the system. Other problems associated with hypothermia are increased risk of infection and bleeding. For these reasons, the CBT is generally closely monitored during medical procedures, or during long-term monitoring of a recovering patient. Conventional methods can involve intrusive probes (oesophageal, rectal, urethral) or active heat-flow sensors that require heating elements and control loops to control the heating elements.

Passive heat-flow sensors that do not require heating elements have the advantage that they are less hazardous to the patient, and consume relatively little power. A conventional heat-flow sensor can only measure heat flow in the outward direction, e.g. outward relative to the surface of the skin to which the sensor is applied. However, core body heat flows in all directions, not just outward from the body. Therefore, a conventional passive heat-flow sensor generally cannot measure core body temperature to the necessary degree of precision unless the sensors are well insulated (which increases the size of the sensor due to the surrounding insulation). Another problem is that the contact area between body and sensor is rarely thermally uniform, particularly since the contact area of the sensor generally needs to be quite large. For example, the temperature profile over a patient's head can exhibit significant differences on account of the positions of the arteries below the skin. A passive heat-flow sensor of the conventional type using two or more vertical thermistor arrangements can provide inaccurate temperature measurements due to poor adhesion of the sensor to the skin, or due to an air pocket between sensor and skin. Such a situation may arise in the case of a wearable sensor worn by a patient while moving around. Furthermore, a conventional heat-flow sensor is quite sensitive to ambient temperature changes.

Therefore, it is an object of the invention to provide an improved heat-flow sensor for measuring the temperature of a subject.

SUMMARY OF THE INVENTION

The object of the invention is achieved by the passive heat-flow sensor of claim 1; by the method of claim 7 of measuring the temperature of a subject using such a passive heat-flow sensor; and by the temperature sensing arrangement of claim 11.

A heat-flow sensor comprises a contact face for placement on a subject during a temperature monitoring procedure. According to the invention, the heat-flow sensor comprises a plurality of combined thermistor arrangements, each comprising an inner thermistor (arranged at an inner face of the sensor) and an upper thermistor (arranged at the upper surface of the sensor) and arranged relative to the inner thermistor to measure a vertical heat flow outward from the subject, i.e. to measure heat flow between the inner thermistor and the upper thermistor; and also a lateral thermistor arranged relative to the inner thermistor to measure a horizontal heat flow along the contact face, i.e. to also measure heat flow between the inner thermistor and the lateral thermistor.

The geometrical terms used in the claims relate to an assumed horizontal plane representing the outer surface of the subject and serve only to define a reference space. A "horizontal heat flow" is therefore any heat flow along the surface of the subject, and a "vertical heat flow" is any heat flow outward from the surface of the subject. It shall be understood that, in reality, a heat-flow sensor can assume any orientation when attached for example to the skin of a patient.

In the context of the invention, the arrangement of one thermistor relative to another is to be understood to mean that these two thermistors are essentially aligned in the direction along which a heat flow is to be measured. Here also, the geometrical terms "upper", "inner" and "outer" are used in the context of the reference space. Therefore, it will be understood that an inner thermistor is arranged at an inner face of the sensor, and an upper thermistor is arranged towards an outer surface of the sensor, such that an upper thermistor is vertically in line with an inner thermistor to measure a heat flow outward from the subject. The outward heat flow is in a direction from an inner thermistor to an upper thermistor when the subject is warmer than the sensor; when the subject is cooler than the sensor the heat flow direction is in reverse. Similarly, it will be understood that a lateral thermistor is arranged in line with an inner thermistor to measure a heat flow along the surface of the subject, for example along the patient's skin. The lateral heat flow is in a direction between the inner thermistor and the lateral thermistor and serves to detect any difference in temperature between the inner sensor region and the side of the sensor containing the lateral thermistor.

An advantage of the heat-flow sensor according to the invention is that the combination of a lateral heat flow monitor with the usual vertical heat flow monitor allows a much more precise temperature measurement, particularly since the lateral heat flow is explicitly measured, instead of only being estimated (as is the case for some conventional heat-flow sensors). The core body temperature of the subject for example a patient during and after surgery can be determined to a much greater degree of precision, so that critical situations such as hypothermia can be detected and dealt with in a timely manner.

According to the invention, the method of measuring the temperature of a subject using such a passive heat-flow sensor comprises the steps of placing the contact face of the heat-flow sensor on the subject during a temperature monitoring procedure; receiving temperature measurements collected by at least one combined thermistor arrangement of the heat-flow sensor; and calculating the temperature of the subject from the temperature measurements.

The inventive method can deliver favorably precise results on account of the additional information provided by the lateral heat flow monitor of the combined thermistor arrangement in the inventive heat-flow sensor. This can be very advantageous in situations for which a precise temperature monitoring is required, for example to provide medical personnel with precise information regarding a patient's core body temperature, for example in an emergency situation requiring rapid decision-making.

According to the invention, the temperature sensing arrangement comprises such a heat-flow sensor and an evaluation unit arranged to receive temperature measurement values from the thermistors and to calculate the temperature of the subject on the basis of the temperature measurement values.

The dependent claims and the following description disclose particularly advantageous embodiments and features of the invention. Features of the embodiments may be combined as appropriate. Features described in the context of one claim category can apply equally to another claim category.

In the context of the invention, the term "subject" can relate to any living being. Critical thermal conditions generally arise in the context of operative situations, emergency medical situations, etc. in which a human patient may enter a state of hypothermia or hyperthermia. Therefore, without restricting the invention in any way, the terms "subject" and "patient" may be regarded as synonymous in the following. The term "heat-flow sensor" as used in the following in the context of the invention may be assumed to refer to a passive heat-flow sensor. Preferably, the passive heat-flow sensor is made of a foam material, and the outer surface of the inventive heat-flow sensor is uniformly exposed to the ambient surroundings. In a further preferred embodiment, a uniform layer of a suitable material in place over the sensor may be used to protect the sensor from damage. However, it should be understood that any thermal influence of such a protective layer will apply in equal measure to each upper thermistor. In other words, the upper thermistors of the inventive passive heat-flow sensor are arranged to be influenced uniformly by the ambient surroundings.

A thermistor is a device whose electrical resistivity changes in response to a change in temperature, and can be embedded in the material of a heat-flow sensor. A thermistor can be realized as a component with two electrical connectors so that it can be included in an appropriate circuit. A temperature change is registered as a change in current or voltage, depending on the circuit realization. A thermistor component can also be realized as a compact integrated circuit (IC) device.

As indicated in the introduction, passive heat-flow sensors using one or more vertical arrangements of thermistor pairs are known from the prior art. The inventive heat flow sensor extends the sensitivity of the temperature measurement by also detecting and measuring a lateral heat flow along the surface of the patient, and the patient's temperature is deduced from the vertical heat flow and lateral heat flow measurements. The inventive heat-flow sensor may be referred to simply as an enhanced heat-flow sensor in the following. In the following, the terms "combined thermistor arrangement" and "enhanced thermistor arrangement" may therefore be used interchangeably. Similarly, the terms "thermistor arrangement" and "thermistor configuration" may be used interchangeably. The term "temperature measurement value" is to be understood as the quantity reported by a thermistor to an evaluation unit, while the term "temperature measurement" relates to the sensed temperature of the subject, i.e. the temperature reported by the evaluation unit of a heat-flow sensor or by the evaluation unit of a temperature sensing arrangement.

The thermal resistivity of the intervening path between two thermistors (inner thermistor and upper thermistor; inner thermistor and lateral thermistor) is determined by structural properties of the temperature monitor such as the material of the sensor and the thickness of the sensor. The thermal resistivity can be measured and can be a known quantity.

For accurate temperature sensing, any inner thermistor of the inventive heat-flow sensor is preferably close to or coincident with the contact face of the sensor. Similarly, any lateral thermistor of an enhanced thermistor configuration is preferably positioned towards an outer region of the sensor and also close to or coincident with the contact face of the sensor. Any upper thermistor is preferably close to the "uppermost" surface of the sensor, i.e. its outside surface when attached to the subject.

In one preferred embodiment of the invention, the thermistors can be connected via wire connections to an evaluation unit. For example, temperature measurement values can be received by an evaluation unit connected to the sensor by a cable connection. In another preferred embodiment of the invention, the sensor can be equipped with an interface for transmitting the temperature measurement values wirelessly to the evaluation module. The sensor may also incorporate an analog-to-digital converter to convert analogue measurement values into digital values for data transmission. The heat-flow sensor of the inventive temperature sensing arrangement can preferably be realized as a wearable device, i.e. a patient can wear the heat-flow sensor for a long-term temperature monitoring interval. An evaluation unit of the inventive temperature sensing arrangement can preferably be realized as a portable device. For example, the patient or any medical personnel can use a hand-held device with a display such as a tablet computer or smart-phone to observe temperature development. In a wearable realization, results of temperature monitoring can be shown on the display of a smart watch or similar device. In a further preferred embodiment of the invention, the temperature sensing arrangement can be incorporated in a patient support device such as an operating table in a surgical operating theatre, a mattress of a hospital bed, an, infant sleeping bag or incubator of a neonatal ward, etc.

In a relatively straightforward embodiment of the inventive heat-flow sensor, a single inner thermistor is used, and this is connected to an upper thermistor and also to a lateral thermistor to achieve the favorable side compensation for accurate estimation of deep body temperature. During a temperature monitoring interval, the temperatures of the three thermistors are observed. The deep body temperature $T_{db}$ (core body temperature) can be expressed as:

$$T_{db} = T1 + \left[ \frac{\frac{T1-T2}{RV} + \frac{T1-T3}{RH}}{R_B} \right] \quad (1)$$

where T1 is the temperature at the inner thermistor; T2 is the temperature at the upper thermistor; T3 is the temperature at the lateral thermistor; RV is the "vertical" thermal resistivity between inner thermistor and upper thermistor; and RH is the "horizontal" thermal resistivity of the electrical connection between inner thermistor and lateral thermistor. $R_B$ is the thermal resistivity of the body to which the sensor is applied, for example skin thermal resistivity. The thermal resistivity of a patient's skin can be estimated, or an already established value can be used by default.

An inner thermistor, common to both vertical and lateral thermistor pairs of an enhanced thermistor configuration, can be located near the center of the sensor, preferably as close as possible to the contact surface. This arrangement may be preferred for a straightforward realization of the inventive heat flow sensor that comprises only a single enhanced thermistor configuration. Such an "enhanced single heat-flow sensor" can provide temperature measurements relating to the outward heat flow from the patient, enhanced or augmented by temperature measurements in one lateral direction along the patient's skin. This configuration already enables a relatively accurate estimation of the patient's core body temperature.

The inventive heat-flow sensor can comprise only such enhanced thermistor arrangements. These can be separate and distinct from each other. Equally, the inventive heat-flow sensor can comprise multiple vertical thermistor pairs, giving a configuration of enhanced thermistor arrangements, each comprising a vertical thermistor pair and the lower thermistor of a neighboring pair. In an alternative embodiment of the invention, the enhanced thermistor arrangements share a single inner thermistor and a single upper thermistor. This enhanced single heat-flow sensor measures heat flow in one vertical direction through the inner and upper thermistors, and augments the vertical heat flow information by additional information obtained by measuring heat flow in several sideways or lateral directions, whereby each lateral direction effectively passes through the inner thermistor and one lateral thermistor. By incorporating more than one lateral thermistor, it is possible to monitor heat flow in more than one lateral direction, allowing a better estimation of the thermal behavior of the area under the sensor contact surface. The lateral thermistor of a combined thermistor arrangement can be a solitary thermistor arranged at the contact face; alternatively the lateral thermistor of a combined thermistor arrangement can be the inner thermistor of a vertical thermistor pair.

In another preferred embodiment, in addition to its enhanced thermistor arrangement(s), the inventive heat-flow sensor comprises a separate vertical thermistor arrangement with a further inner thermistor and a further upper thermistor arranged relative to that inner thermistor to measure a further vertical heat flow outward from the subject. This additional vertical thermistor arrangement is functionally independent of any combined thermistor arrangement, and such an embodiment may be referred to as an enhanced dual heat-flow sensor. Preferably, the vertical thermistor arrangement is positioned centrally in the heat-flow sensor. A centrally positioned and independent vertical thermistor arrangement can be flanked by a plurality of equidistantly arranged enhanced thermistor configurations, for example.

In an embodiment comprising a vertical thermistor arrangement and one enhanced thermistor arrangement, it is not necessary to know the thermal resistivity of the skin, since this term cancels out of the equation for deep body temperature $T_{db}$, which is now expressed as:

$$T_{db} = \frac{T1(TV1 - TV2) + K \cdot TV1(T2 - T1) + L \cdot TV1(T3 - T1)}{TV1 - TV2 + K(T2 - T1) + L(T3 - T1)} \quad (2)$$

where TV1 is the temperature at the inner thermistor of the vertical thermistor arrangement and TV2 is the temperature at the upper thermistor of the vertical thermistor arrangement; T1 is the temperature at the inner thermistor of the enhanced heat-flow thermistor arrangement, T2 is the temperature at the upper thermistor of the enhanced thermistor arrangement, and T3 is the temperature at the outer or lateral thermistor of the enhanced thermistor arrangement. K and L are scalar values. The value K is expressed as:

$$K = -\frac{(TV1 - TV2)(T1 - T_{db})}{(-3T1 + T2 + 2T3)(TV1 - T_{db})} \quad (3)$$

The scalar value L is a ratio and can be expressed as:

$$L = \frac{RV2}{RH} \quad (4)$$

where RV2 is the thermal resistivity between inner and upper thermistors of the vertical thermistor arrangement; and RH is the thermal resistivity between inner and lateral thermistors of the enhanced thermistor arrangement.

In one exemplary embodiment, for which the vertical thermal resistivity RV of the enhanced thermistor arrangement is twice the horizontal thermal resistivity RH, equation (4) reduces to:

$$L = \frac{RV1}{RH} = \frac{RV1}{0.5RV} = \frac{2RV1}{RV} = 2K \quad (5)$$

This allows equation (2) to be solved for the value of deep body temperature $T_{db}$.

In a particularly preferred embodiment of the invention, the heat-flow sensor comprises multiple enhanced thermistor arrangements. Similar equations on the basis of equations (2)-(5) above can be developed for embodiments of the inventive enhanced heat-flow sensors that two or more enhanced thermistor arrangements. The evaluation unit can comprise a microprocessor or functional equivalent, realized to execute one or more algorithms, based on the above equations that process the temperature measurement values delivered by the thermistors in order to compute a deep body or core temperature of the subject.

An advantage of measuring heat flow in more than one lateral direction is that it allows a precise temperature measurement even if the heat-flow sensor is not ideally or optimally in position. It can often be difficult to exactly determine a correct or ideal sensor placement, for example when a sensor is to be placed over the carotid artery. A slightly "off-center" placement could result in significant errors in temperature measurements when a prior art heat-flow sensor is used. An inventive heat-flow sensor with several enhanced thermistor configurations provides several candidate temperature measurement values, from which a more precise core body temperature can be deduced. For example, in a preferred embodiment of the invention, temperature measurements are received from a plurality of combined thermistor arrangements, and the temperature measurements are averaged before calculating the temperature of the subject. Equally, the maximum temperature value reported by a thermistor may be used for the calculation of lateral and vertical flows. For example, the temperature measurement values received from the sensor can be examined to identify the pair of inner and outer thermistors that shows the maximum vertical heat flow. This vertical thermistor pair will generally be characterized by the inner thermistor that has the greatest temperature measurement value, for example. Then, the vertical thermistor pairs (or the lateral thermistors) that neighbor that "maximum vertical flow" thermistor pair are identified. Their temperature measurement values are then used to establish a lateral heat flow outward from the "maximum vertical flow" thermistor pair.

Another advantage of using several enhanced thermistor configurations is given by the ability to identify an enhanced thermistor configuration that is sub-optimally placed to measure temperature. The inventive method preferably comprises the steps of comparing temperature measurements from a plurality of enhanced thermistor configurations; identifying an enhanced thermistor configuration that is providing unreliable temperature measurement values; and discarding those temperature measurement values.

For example, a situation might arise in which the sensor is not ideally attached to the skin of the patient. In a heat-flow sensor with three or more equidistantly arranged enhanced thermistor configurations, any significant difference between the values delivered by the enhanced thermistor configurations can be identified. If one of the enhanced thermistor configurations delivers vales that are significantly different from the values delivered by the other enhanced thermistor configurations, and if the values delivered by the other enhanced thermistor configurations are relatively similar, this would indicate that the sensor is not adequately attached to the skin. Any thermistor delivering outlier or non-conformant values is preferably disregarded so that its data does not falsify computation of the core body temperature.

In both sensors when using the side thermometer the estimated CBT is less sensitive to environmental changes and gives good results, whereas the basic single and dual heat-flow CBT sensors without a side thermometer are sensitive to the environmental changes. Including a side thermistor improves the estimated CBT during a variation of the core body temperature as well as during a variation of environmental changes.

Other objects and features of the present invention will become apparent from the following detailed descriptions considered in conjunction with the accompanying drawings. It is to be understood, however, that the drawings are designed solely for the purposes of illustration and not as a definition of the limits of the invention.

BRIEF DESCRIPTION OF THE DRAWINGS

FIG. 1 is a schematic representation of a first embodiment of the inventive temperature sensing arrangement;

FIG. 2 shows a plan view of the heat-flow sensor of FIG. 1 from below;

FIG. 3 shows a plan view of the heat-flow sensor of FIG. 1 from above;

FIG. 4 shows temperature curves relating to the heat-flow sensor of FIG. 1;

In the drawings, like numbers refer to like objects throughout. Objects in the diagrams are not necessarily drawn to scale.

DETAILED DESCRIPTION OF THE EMBODIMENTS

Figure 5:
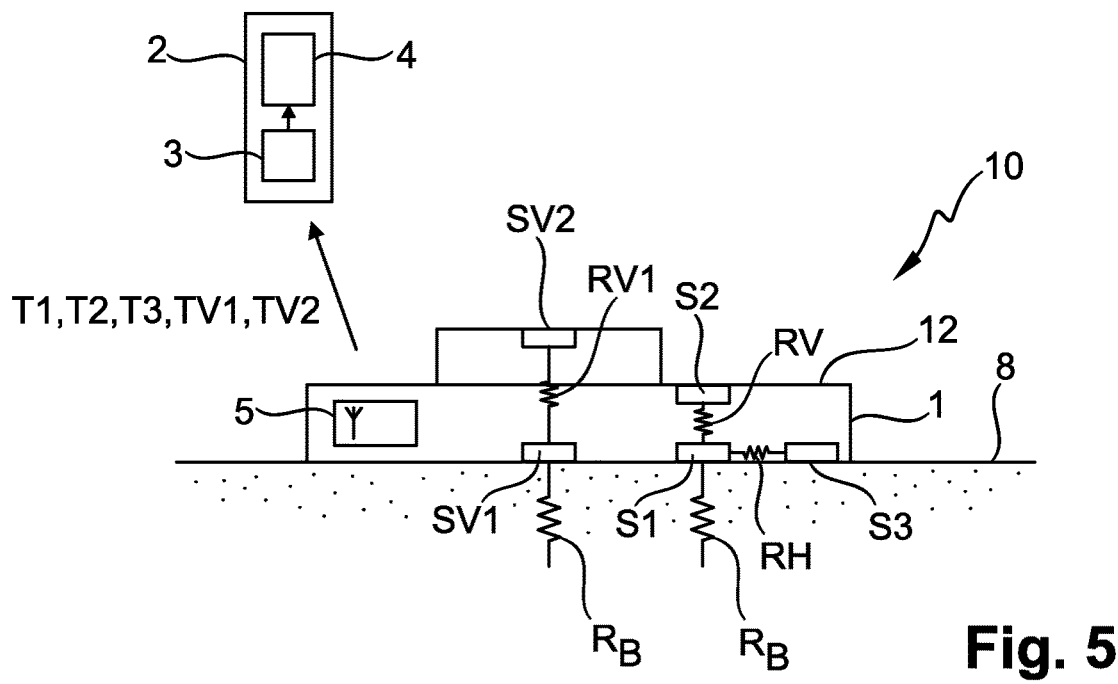
FIG. 5 is a schematic representation of a second embodiment of the inventive temperature sensing arrangement.

FIG. 1 shows a schematic cross-section through the inventive heat-flow sensor 1, realized in this exemplary embodiment as an enhanced single heat-flow sensor 1 of a temperature monitoring arrangement 10. This can be securely attached to the subject 8, for example to the skin of a patient 8. The outer surface 12 of the sensor is exposed to the surroundings and is not covered by any insulating material. A first thermistor S1 is arranged at an inner face of the sensor 1, and will lie in close contact to the patient's skin. A second thermistor S2 is arranged at the upper surface of the sensor 1. The thermal resistivity RV of the sensor 1 in the "vertical" direction, and the thermal resistivity RH of the sensor 1 in the "horizontal" direction are indicated by resistor symbols. A further resistor symbol indicates the thermal resistivity $R_B$ of the body 8 to which the sensor 1 is attached.

Obtaining a temperature measurement at any one point in time using the sensor 1 involves collecting the temperature measurement values T1, T2, T3 from the thermistors S1, S2, S3 respectively (i.e. thermistor S1 delivers temperature measurement value T1, thermistor S2 delivers temperature measurement value T2 etc.) and calculating a sensed temperature using knowledge of the heat flux through the sensor 1. To compute the sensed temperature using the enhanced single heat-flow sensor 1, it is also necessary to determine or estimate the thermal resistivity $R_B$ of the skin, which may vary from patient to patient. The sensed body temperature $T_{db}$ may be calculated using equation (1) as already described above. To this end, the measurement values collected by the thermistors S1, S2, S3 are sent to an evaluation unit 2 of the temperature monitoring arrangement 10, for example over a cable connection or wirelessly. A microprocessor 3 of the evaluation unit 2 performs the necessary computations to arrive at the body temperature. A display 4 can show core body temperature development as time progresses. While the diagram only indicates one lateral thermistor for the sake of simplicity, any number of lateral thermistors S3 and vertical thermistor pairs S1, S2 can be implemented by such an enhanced single heat-flow sensor.

FIG. 2 shows a plan view of such a sensor from below, showing the positions of an inner thermistor S1 and lateral thermistors S3 on the contact face 11 of the sensor 1. In this exemplary embodiment, the sensor 1 comprises a centrally positioned inner thermistor S1, and four equidistantly arranged lateral thermistors S3. FIG. 3 shows a plan view of the sensor 1 from above, indicating the position of the upper thermistor S2 of the enhanced thermistor configuration. The shape of the sensor does not have to be circular with a flat contact surface, as shown in the exemplary embodiments, but can be chosen to best fit the region on the body where the sensor is to be used.

FIG. 4 shows temperature curves obtained in a basic test setup, using a hotplate with a set point at 37° C., and a skin-like material with a thermal conductivity of 0.30 W/mK. A first curve 40 shows the temperature of the body measured using the inventive enhanced single heat-flow sensor, with a single enhanced thermistor arrangement. A second curve 41 shows the temperature measured using a conventional single heat-flow sensor (without any lateral compensation). The advantage of using the lateral thermistor can clearly be seen, since the temperature estimated using values provided by the enhanced thermistor arrangement reaches equilibrium faster, and is a closer match to the reference temperature.

FIG. 5 shows a schematic cross-section through a second embodiment of the inventive heat-flow sensor 1. Here, the sensor 1 comprises a lower layer and an upper layer, to achieve two different values of thermal resistivity RV, RV1 in the vertical or outward direction. The diagram shows an enhanced thermistor configuration with thermistors S1, S2, S3 as described in FIG. 1 above, and also an additional vertical thermistor configuration comprising a further inner thermistor SV1 and a further outer thermistor SV2. Here, thermistor SV1 delivers temperature measurement value TV1, and thermistor SV2 delivers temperature measurement value TV2. In this embodiment, the temperature measurement values T1, T2, T3 from the enhanced thermistor configuration and the temperature measurement values TV1, TV2 from the additional vertical thermistor configuration are sent to an evaluation unit 2, which can be realized in a hand-held device such as a smartphone or tablet computer with a display 4. A microprocessor 3 of the hand-held device can compute the body temperature $T_{db}$ using equations (2)-(5) as described above. In this exemplary embodiment, the sensor 1 comprises a wireless interface 5 for wireless transmission of the temperature measurement values T1, T2, T3, TV1, TV2 to the evaluation unit 2.

Figure 6:
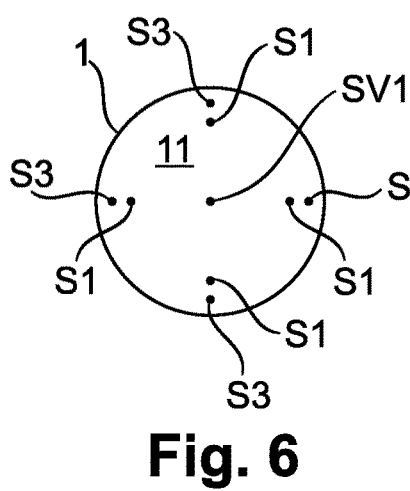
FIG. 6 shows a plan view of the heat-flow sensor of FIG. 5 from below.
Figure 7:
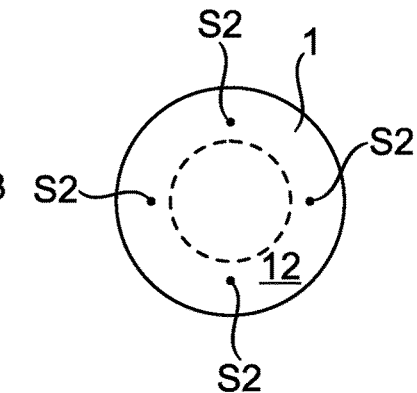
FIG. 7 shows a plan view of the heat-flow sensor of FIG. 5 from above, showing a middle level.
Figure 8:
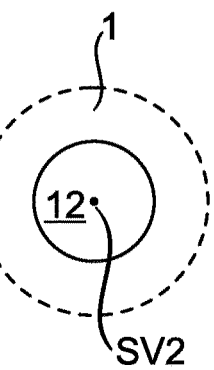
FIG. 8 shows a plan view of the heat-flow sensor of FIG. 5 from above, showing a top level.

FIG. 6 shows a plan view from below of an enhanced dual-flow sensor 1 with four enhanced thermistor configurations about a central vertical thermistor configuration, indicating the position of the inner thermistor SV1 of the centrally positioned vertical thermistor configuration, the positions of the inner thermistors S1 and the lateral thermistors S3 of the four enhanced thermistor configurations. FIG. 7 shows a plan view from above the middle layer of the enhanced dual-flow sensor 1, indicating the positions of the upper thermistors S2 of the enhanced thermistor configurations. FIG. 8 shows a plan view from above the top layer of the enhanced dual-flow sensor 1, indicating the position of the upper thermistor SV2 of the centrally positioned vertical thermistor configuration. Temperature measurement values provided by the four enhanced thermistor configurations can be averaged to improve the accuracy of the sensed body temperature.

Figure 9:
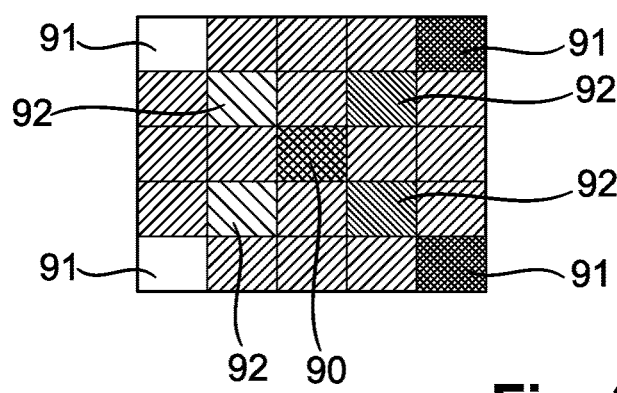
FIG. 9 shows temperature regions relating to the sensor of FIG. 5.

FIG. 9 shows a schematic representation of the temperatures corresponding to the thermistor arrangements of the enhanced dual-flow sensor of FIGS. 6-8. Here, the relative temperatures of the various thermistor arrangements are indicated as shaded regions 90, 91, 92 of a matrix. The intensity of the shading is interpreted relative to the remaining neutral regions of the matrix. The temperature measured by the vertical thermistor arrangement is indicated by the central shaded region 90. Temperatures measured using data provided by the inner and upper thermistors of the enhanced thermistor arrangements are indicated by the shaded regions 92, while the temperatures measured using data provided by the inner and lateral thermistors of the enhanced thermistor arrangements are indicated by the shaded regions 91. The darker color of the shaded region at the upper right in the diagram indicates that this thermistor is in poor contact with the patient's skin. The evaluation unit can identify such a discrepancy in the temperature measurement values, and can choose to ignore temperature measurement values from a thermistor configuration that appears to be delivering erroneous or unreliable data.

Figure 10:
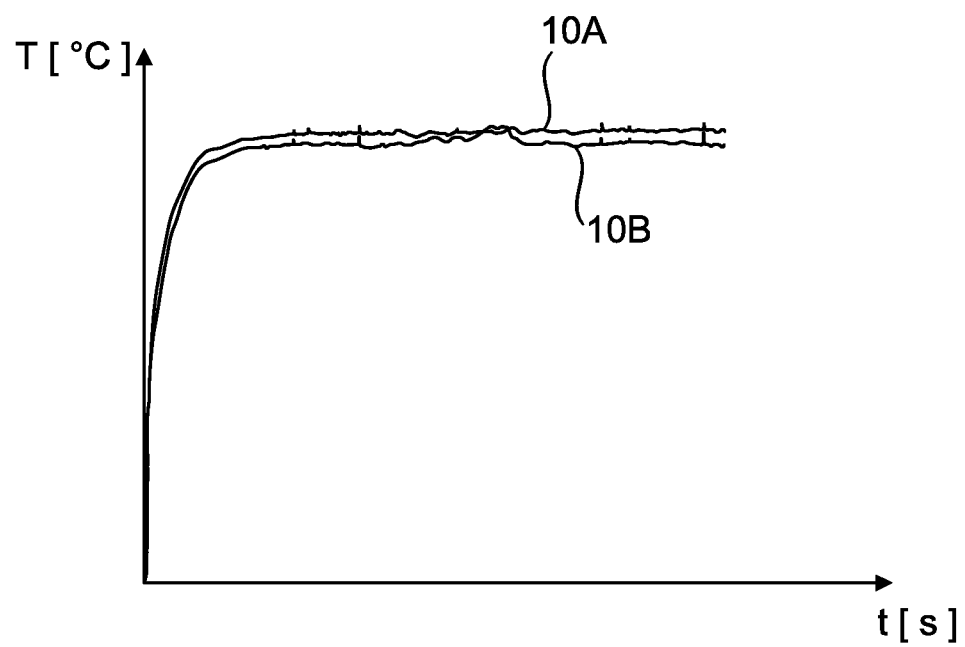
FIG. 10 shows temperature development of enhanced thermistor configurations in an inventive sensor of the dual heat-flow type.

FIG. 10 shows an exemplary temperature development plot of the enhanced thermistor arrangements described in FIG. 9 above. Curve 10A is exemplary of a temperature calculated on the basis of temperature measurement values from three enhanced thermistor arrangements of which the inner thermistors are in good contact with the patient's skin. Curve 10B is exemplary of a temperature calculated on the basis of temperature measurement values from a fourth enhanced thermistor arrangement of which the inner thermistors are in poor contact with the patient's skin. Owing to the persistent significant difference in the values, the evaluation unit would disregard the values provided by the fourth enhanced thermistor arrangement from the temperature calculation algorithm.

The final estimated core body temperature depends to a large extent on the geometry and thermal conductivity of the sensor. Experimental results have shown that even during sub-optimal conditions, the enhanced sensor performs very well. When applied to a reference body that is gradually heated, the temperature sensed using data provided by an inventive enhanced single heat-flow sensor is a much closer match than the temperature sensed using data provided by the conventional single heat-flow sensor. Similarly, the temperature sensed by an enhanced dual heat-flow sensor according to the invention has been observed to be more precise than a comparable conventional dual sensor, which although considered to be quite accurate can report sensed temperatures that are off by about 0.4° C. This is considered to be a significant discrepancy regarding core body temperature, particularly when it is necessary to identify a tendency towards hypothermia or hyperthermia so that preventive measures can be taken to avoid a critical situation.

The improvement in accuracy of the inventive enhanced heat-flow sensor is because it considers lateral heat flow also, and is therefore significantly less sensitive to variations in ambient temperature. The improvement in accuracy has been observed for a reference body with a constant temperature at 37.5° C. and a variation in the ambient or outside temperature from 0° C. to 30° C. The body temperature as measured by the inventive enhanced heat-flow sensor remains essentially constant for all values of ambient temperature, whereas a comparable conventional heat-flow sensor exhibits relatively poor performance particularly at the lower temperatures, The enhanced heat-flow sensor according to the invention performs significantly better than its conventional counterpart which does not.

Figure 11:
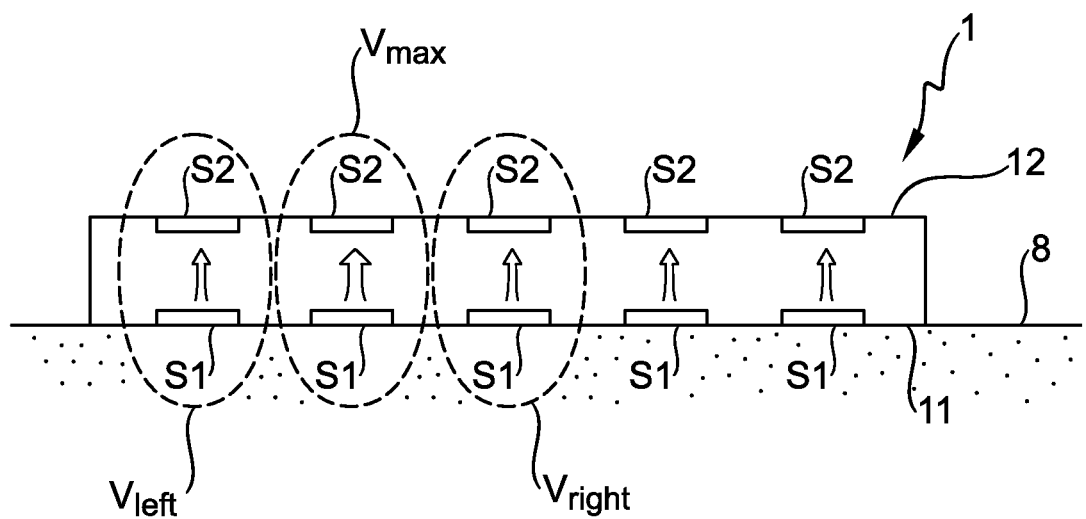
FIG. 11 is a schematic representation of a third embodiment of the inventive temperature sensing arrangement.

FIG. 11 shows a further embodiment of the inventive passive heat-flow sensor, realized as a single heat-flow sensor and comprising vertical thermistor pairs S1, S2, giving a configuration of enhanced thermistor arrangements, each comprising a vertical thermistor pair S1, S2 and a lateral thermistor corresponding to the lower thermistor S1 of a neighboring vertical thermistor pair. To determine the core body temperature, the temperature measurement values of the thermistors S1, S2 are examined to identify the pair $V_{max}$ with the maximum vertical heat flow. Of this vertical thermistor pair $V_{max}$, the inner thermistor S1 and outer thermistor S2 will supply the values for T1 and T2 of equation (2) above. A value of T3 can be determined by obtaining the mean temperature of a neighboring vertical pair, for example the vertical pair $V_{left}$ on the left of the "maximum vertical flux" pair $V_{max}$ or the vertical pair $V_{right}$ on the right, etc. by adding the temperature measurement values of the thermistors S1, S2 and halving the result. The most likely result can be chosen as the value for T3 in equation (2) above.

Figure 12:
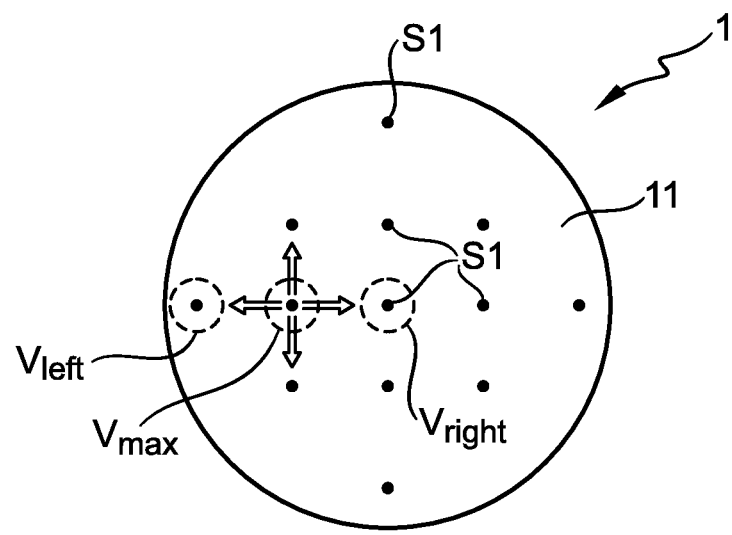
FIG. 12 shows a plan view of the heat-flow sensor of FIG. 11 from below.

FIG. 12 shows a plan view of the single heat-flow sensor of FIG. 11, showing its contact face 11. The positions of the inner thermistors S1 are shown. The location of the thermistor pair $V_{max}$ with the maximum vertical heat flow is indicated by the dotted line encircling the corresponding inner thermistor. The diagram shows that this thermistor pair $V_{max}$ has four possible "neighbors" (two such pairs $V_{left}$, $V_{right}$ were described in FIG. 11), any of which can be used to determine a value of T3 as described above. The advantage of being able to choose between multiple neighboring thermistors is that any erroneous temperature measurement values (arising from sub-optimal contact to the patient's skin, for example) can be identified and disregarded, as explained in FIG. 9 above.

Although the present invention has been disclosed in the form of preferred embodiments and variations thereon, it will be understood that numerous additional modifications and variations could be made thereto without departing from the scope of the invention. For example, any suitable sensor shape may be used. Equally, different numbers of vertical and lateral thermistors can be incorporated in various embodiments of the inventive enhanced heat-flow sensor. As described above, calculation of core temperature can be performed on the sensor or can be performed remotely. Results can be displayed locally (on a screen) or remotely on a smart watch, mobile phone or the display of any other suitable device. Furthermore, the principle of the invention can be used in an active sensor realization, for example by controlling a heating element to bring the sensor to a zero heat-flux state.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

REFERENCE SIGNS 1 heat-flow sensor
2 evaluation unit
3 microprocessor
4 display
5 wireless interface
8 subject
10 temperature sensing arrangement
11 sensor contact face
12 sensor outer surface
10A, 10B temperature curve
40, 41 temperature curve
90, 91, 92 matrix field
110, 111 temperature curve
120, 121 temperature curve
130, 131, 132 temperature curve
140, 141 temperature curve
$R_B$ body resistivity
RV, RV1, RH thermal resistivity
S1, SV1 inner thermistor
S2, SV2 upper thermistor
S3 lateral thermistor
$T_{db}$ core body temperature
T1, T2, T3 temperature measurement value
TV1, TV2 temperature measurement value
$V_{max}$ thermistor pair
$V_{left}$, $V_{right}$ thermistor pair

The invention claimed is:

1. A passive heat-flow sensor comprising a contact face for placement on a subject during a temperature monitoring procedure; and a plurality of combined thermistor arrangements, wherein a combined thermistor arrangement comprises:
   an inner thermistor arranged at an inner face of the sensor;
   an upper thermistor arranged at the upper surface of the sensor and arranged relative to the inner thermistor to measure a vertical heat flow outward from the subject wherein the combined thermistor arrangement is positioned centrally in the heat-flow sensor; and
   at least three lateral thermistors arranged radially and equidistantly spaced about the inner thermistor and the upper thermistor, the at least three lateral thermistors arranged to measure a horizontal heat flow along the contact face.

2. A passive heat-flow sensor according to claim 1, comprising at least four combined thermistor arrangements.

3. A passive heat-flow sensor according to claim 1, wherein an outer surface of the sensor is exposed.

4. A passive heat-flow sensor according to claim 1, realized as a passive dual heat-flow sensor and comprising a vertical thermistor arrangement with a further inner thermistor and a further upper thermistor arranged relative to that inner thermistor to measure a further vertical heat flow outward from the subject.

5. A method of measuring the temperature of a subject using a passive heat-flow sensor according to claim 1, which method comprises the steps of:
   placing the contact face of the passive heat-flow sensor on the subject during a temperature monitoring procedure;
   receiving temperature measurement values collected by the thermistors of the passive heat-flow sensor;
   calculating the temperature of the subject on the basis of the received temperature measurement values;
   comparing temperature measurement values of the combined thermistor arrangements of the passive heat-flow sensor;
   identifying a combined thermistor arrangement providing unreliable temperature measurement values; and
   discarding temperature measurement values collected by that combined thermistor arrangement.

6. A method of measuring the temperature of a subject using a passive heat-flow sensor according to claim 1, which method comprises the steps of:
   placing the contact face of the passive heat-flow sensor on the subject during a temperature monitoring procedure;
   receiving temperature measurement values collected by the thermistors of the passive heat-flow sensor;
   comparing temperature measurement values of the combined thermistor arrangements of the passive heat-flow sensor to identify thermistors associated with a maximum vertical heat flow;
   identifying the neighboring combined thermistors; and
   calculating the temperature of the subject on the basis of the temperature measurement values of the neighboring combined thermistors.

7. A method according to claim 6, comprising the step of averaging one or more temperature measurement values prior to calculating the temperature of the subject.

8. A temperature sensing arrangement for monitoring the temperature of a subject, comprising:
   a passive heat-flow sensor according to claim 1; and an evaluation unit arranged to receive temperature measurement values from the thermistors of the passive heat-flow sensor and to calculate the temperature of the subject on the basis of the received temperature measurement values.

9. A temperature sensing arrangement according to claim 8, wherein the passive heat-flow sensor comprises a wireless interface for transmitting temperature measurement values to the evaluation unit.

10. A temperature sensing arrangement according to claim 8, wherein the passive heat-flow sensor is realized as a wearable device.

11. A temperature sensing arrangement according to claim 8, wherein the evaluation unit is realized as a portable device.

12. A temperature sensing arrangement according to claim 8, incorporated in a patient support device.

* * * * *